United States Patent
Kanou et al.

(10) Patent No.: US 10,556,794 B2
(45) Date of Patent: Feb. 11, 2020

(54) DESORBING PROCESS, HYDROGEN-SUPPLYING SOLUTION, AND DESORBING APPARATUS

(71) Applicant: Panasonic Intellectual Property Management Co., Ltd., Osaka (JP)

(72) Inventors: Manabu Kanou, Osaka (JP); Yuki Nakata, Osaka (JP); Yuji Zenitani, Nara (JP); Hyunjeong Nam, Nara (JP); Saifullah Badar, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 236 days.

(21) Appl. No.: 15/612,475

(22) Filed: Jun. 2, 2017

(65) Prior Publication Data

US 2017/0362085 A1    Dec. 21, 2017

(30) Foreign Application Priority Data

Jun. 20, 2016  (JP) ................................ 2016-121430
Jan. 24, 2017  (JP) ................................ 2017-010454

(51) Int. Cl.
| | | |
|---|---|---|
| C01B 3/00 | (2006.01) | |
| C07C 5/32 | (2006.01) | |
| C25B 3/00 | (2006.01) | |
| C25B 3/02 | (2006.01) | |

(52) U.S. Cl.
CPC .............. C01B 3/0015 (2013.01); C07C 5/32 (2013.01); C25B 3/02 (2013.01)

(58) Field of Classification Search
CPC ................ C01B 3/00; C07C 5/32; C25B 3/02
See application file for complete search history.

(56) References Cited

U.S. PATENT DOCUMENTS

| | | |
|---|---|---|
| 2011/0171119 A1 | 7/2011 | Yazami |
| 2015/0259200 A1 | 9/2015 | Kalb |

FOREIGN PATENT DOCUMENTS

| | | | |
|---|---|---|---|
| JP | 2005-211845 | 8/2005 | |
| JP | 2015-147998 A | 8/2015 | |
| JP | 2015147998 | * 8/2015 | ............. C25B 13/04 |

OTHER PUBLICATIONS

Driscoll et al. (Redox catalysis for dehydrogenation of liquid hydrogen carrier fuels for energy storage and conversion, ECS Transactions, 35 (28) 3-17, 2011) (Year: 2011).*
Panasonic (JP 2015-147998_ English Translation (Year: 2015).*
Masaru Ichikawa, "Book for understanding hydrogen energy, hydrogen society and hydrogen business", Ohmsha Ltd., pp. 108-109, Feb. 5, 2007. (Partial Translation).
(Continued)

Primary Examiner — Youngsul Jeong
(74) Attorney, Agent, or Firm — McDermott Will & Emery LLP

(57) ABSTRACT

The desorbing process of the present disclosure includes a step of bringing a solution containing a hydrogenated aromatic compound, at least one of $[P((CH_2)_mCH_3)_3((CH_2)_nCH_3)\ (5 \leq m \leq 24,\ 13 \leq n \leq 24)]^+$ and $[N((CH_2)_mCH_3)_3((CH_2)_nCH_3)\ (5 \leq m \leq 24,\ 13 \leq n \leq 24)]^+$, and an anion into contact with an anode; and desorbing hydrogen from the hydrogenated aromatic compound.

5 Claims, 8 Drawing Sheets

(56) References Cited

OTHER PUBLICATIONS

Peter F. Driscoll et al., "Electrochemical Redox Catalysis for Electrochemical Dehydrogenation of Liquid Hydrogen Carrier Fuels for Energy Storage and Conversion", Journal of the Electrochemical Society,160, G3152-G3158, May 11, 2013.

Peter F. Driscoll et al., "Redox Catalysis for Dehydrogenation of Liquid Hydrogen Carrier Fuels for Energy Storage and Conversion", ECS Transactions, 35 (28) 3-17 (2011), Oct. 11, 2011.

The Extended European Search Report dated Oct. 17, 2017 for the related European Patent Application No. 17173489.0.

The Extended European Search Report dated Oct. 18, 2017 for the related European Patent Application No. 17173923.8.

N.Dost et al: "The dehydrogenation of hydrocarbons by means of quinones: I. action of Chloranil", Recueil Des Travaux Chimiques Des Pays-Bas, vol. 70, No. 5, Jan. 1, 1951 (Jan. 1, 1951), pp. 403-411, XP055411540.

P. N. Pintauro et al: "The role of supporting electrolyte during the electrocatalytic hydrogenation of aromatic compounds", Journal of App li ed Electrochemistry., vol. 21, No. 9, Sep. 1, 1991 (Sep. 1, 1991), pp. 799-804, XP055220681.

\* cited by examiner n = 1 n = 2 n = 3

DESORBING PROCESS, HYDROGEN-SUPPLYING SOLUTION, AND DESORBING APPARATUS

BACKGROUND

1. Technical Field

The present disclosure relates to an desorbing process, a hydrogen-supplying solution, and an desorbing apparatus.

2. Description of the Related Art

In recent years, technologies utilizing hydrogen energy have been actively studied. For example, fuel cells for domestic or industrial use and fuel cell vehicles have been put to practical use. Unlike electric energy, in principle, hydrogen can be stored as it is. However, since hydrogen is a gas at normal temperature and pressure, in particular, the volume density of the energy is small. Accordingly, hydrogen is, for example, stored in a hydrogen cylinder under pressure, maintained in a liquid state, or occluded in a hydrogen storage alloy.

"Suiso enerugi ga wakaru hon Suiso shakai to suiso bizinesu (Easy book for understanding hydrogen energy— Hydrogen society and Hydrogen business (Ohmsha, Ltd.)" proposes an organic hydride method as a hydrogen-storing method different from the above-mentioned methods. In the organic hydride method, hydrogen is stored in a state being bound to an aromatic compound. For example, hydrogen is bound to toluene to generate methylcyclohexane, and hydrogen is stored in the state of methylcyclohexane. Methylcyclohexane returns to toluene by desorbing hydrogen. Similarly, hydrogen can be stored by utilizing the conversion between naphthalene and decahydronaphthalene (decalin).

In the organic hydride method, the compound to which hydrogen is bound and the compound from which hydrogen is desorbed are liquid at normal temperature and can be treated as compounds belonging to petroleum, such as gasoline and kerosene. Since these compounds are stable and recyclable and therefore seem to be useful as hydrogen storing and supplying means.

However, in the organic hydride method, since the hydrogen desorption reaction is an endothermic reaction, energy from the outside is necessary for desorbing hydrogen. Accordingly, catalysts capable of desorbing hydrogen with less thermal energy have been studied (Japanese Unexamined Patent Application Publication No. 2005-211845). Peter F. Driscoll, Elise Deunf, Leah Rubin, John Arnold, John B. Kerr, Journal of Electron Society, 160 G3152-G3158 (2013) proposes a method of electrochemically desorbing hydrogen.

However, the electrochemical reactions of organic hydrides need further improvement.

SUMMARY

One non-limiting and exemplary embodiment provides an desorbing process of an organic hydride, a hydrogen-supplying solution, and an desorbing apparatus.

In one general aspect, the techniques disclosed here feature an desorbing process including bringing a solution containing a hydrogenated aromatic compound, at least one of $[P((CH_2)_mCH_3)_3((CH_2)_nCH_3)]^+$ ($5 \leq m \leq 24$, $13 \leq n \leq 24$)]$^+$ and $[N((CH_2)_mCH_3)_3((CH_2)_nCH_3)]^+$ ($5 \leq m \leq 24$, $13 \leq n \leq 24$)]$^+$ and an anion to anode; and desorbing hydrogen from the hydrogenated aromatic compound.

The desorbing process, the hydrogen-supplying solution, and the desorbing apparatus of the present disclosure can provide a reaction system that can utilize an electrochemical reaction of an organic hydride.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
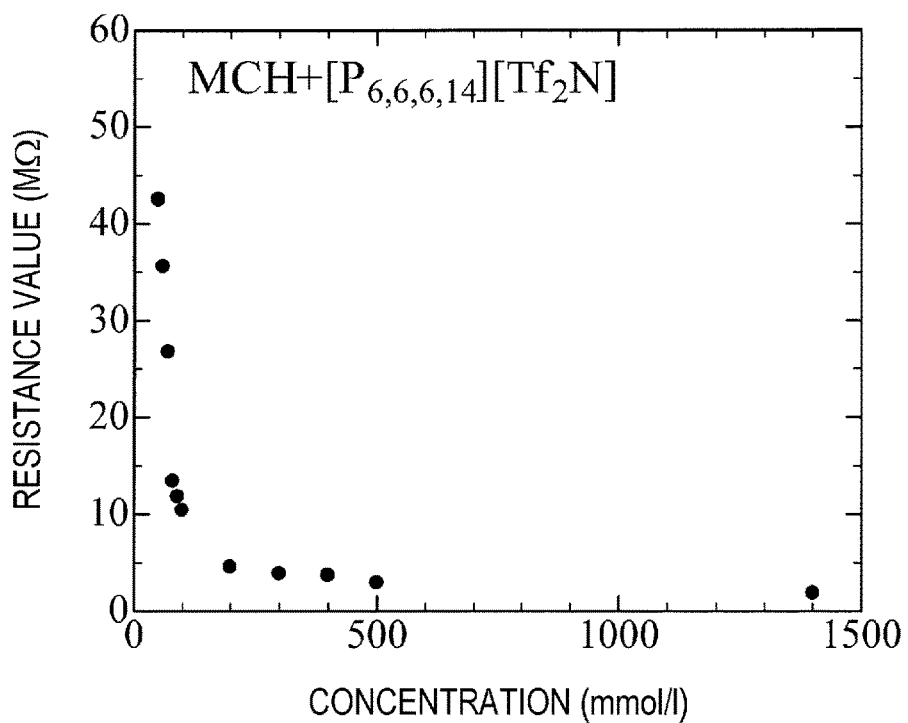
FIG. 1 is a graph showing the concentration dependence of resistance value when an electrolyte is dissolved in a hydrogenated aromatic compound.

In order to proceed a variety of electrochemical reactions of organic hydrides including electrochemical dehydrogenation as described above, it is necessary to perform electrochemical electron transfer with an organic hydride or a material capable of reacting with an organic hydride. Accordingly, the organic hydride or a liquid containing the organic hydride preferably has conductivity.

However, the organic hydrides that are used for storing hydrogen are generally composed of only carbon and hydrogen, and the organic hydride molecules have low polarity. Consequently, a common electrolyte is not dissolved in such an organic hydride at a sufficient concentration when the common electrolyte is used for imparting conductivity to the organic hydride.

In order to increase the concentration of an electrolyte in an organic hydride, it is conceivable to add a polar solvent to the organic hydride. However, in this case, the ratio of the organic hydride in the liquid is decreased to reduce the storage density of hydrogen energy. The present disclosure provides an desorbing process of an organic hydride, a hydrogen-supplying solution, and an desorbing apparatus. The outlines of the desorbing process, the hydrogen-supplying solution, and the desorbing apparatus of the present disclosure are as follows.

The desorbing process of a first aspect of the present disclosure includes steps of: bringing a solution containing a hydrogenated aromatic compound, at least one of $[P((CH_2)_mCH_3)_3((CH_2)_nCH_3)$ $(5 \leq m \leq 24, 13 \leq n \leq 24)]^+$ and $[N((CH_2)_mCH_3)_3((CH_2)_nCH_3)$ $(5 \leq m \leq 24, 13 \leq n \leq 24)]^+$, and an anion into contact with an anode; and desorbing hydrogen from the alicyclic saturated hydrocarbon.

In the desorbing process of a second aspect of the present disclosure, the hydrogenated aromatic compound in the desorbing process according to the first aspect may include at least one selected from the group consisting of cyclohexane, methylcyclohexane, dimethylcyclohexane, and decalin.

In the desorbing process of a third aspect of the present disclosure, the solution in the desorbing process according to the first or second aspect may contain $[P((CH_2)_5CH_3)_3((CH_2)_{13}CH_3)]^+$ or $[N((CH_2)_5CH_3)_3((CH_2)_{13}CH_3)]^+$ at a concentration of 100 mmol/L or more.

In the desorbing process of a fourth aspect of the present disclosure, the anion in the desorbing process according to any one of the first to third aspects may include at least one of $[N(SO_2CF_3)_2]^-$ and $[[(CH_3)_3CCH_2CH(CH_3)CH_2]PO_2]^-$.

In the desorbing process of a fifth aspect of the present disclosure, the desorbing process according to any one of the first to fourth aspects may include a step of bringing the solution into contact with a cathode and may desorb hydrogen from the hydrogenated aromatic compound in the step of applying a voltage to the solution.

The hydrogen-supplying solution of a sixth aspect of the present disclosure contains a hydrogenated aromatic compound, at least one of $[P((CH_2)_mCH_3)_3((CH_2)_nCH_3)$ $(5 \leq m \leq 24, 13 \leq n \leq 24)]^+$ and $[N((CH_2)_mCH_3)_3((CH_2)_nCH_3)$ $(5 \leq m \leq 24, 13 \leq n \leq 24)]^+$, and an anion.

In the hydrogen-supplying solution of a seventh aspect of the present disclosure, the hydrogenated aromatic compound in the hydrogen-supplying solution according to the sixth aspect may include at least one selected from the group consisting of cyclohexane, methylcyclohexane, dimethylcyclohexane, and decalin.

In the hydrogen-supplying solution of an eighth aspect of the present disclosure, the hydrogen-supplying solution according to the sixth or seventh aspect may contain $[P((CH_2)_5CH_3)_3((CH_2)_{13}CH_3)]^+$ or $[N((CH_2)_5CH_3)_3((CH_2)_{13}CH_3)]^+$ at a concentration of 100 mmol/L or more.

In the hydrogen-supplying solution of a ninth aspect of the present disclosure, the anion in the hydrogen-supplying solution according to any one of the sixth to eighth aspects may include at least one of $[N(SO_2CF_3)_2]^-$ and $[[(CH_3)_3CCH_2CH(CH_3)CH_2]PO_2]^-$.

The desorbing apparatus of a tenth aspect of the present disclosure includes a hydrogen-supplying solution according to any one of the sixth to ninth aspects, a storage chamber containing the hydrogen-supplying solution, an anode, and a cathode.

Embodiments of the desorbing process, the hydrogen-supplying solution, and the desorbing apparatus of the present disclosure will now be described with reference to the drawings. The desorbing process of the present disclosure includes a step of applying a voltage to a hydrogen-supplying solution. The term "hydrogen-supplying solution" refers to a liquid containing desorbable hydrogen atoms or molecules and being capable of generating hydrogen by a desorption reaction.

The embodiments described below all show comprehensive or specific examples. The numbers, shapes, materials, components, arrangement positions and connection configuration of the components, etc. shown in the following embodiments are merely examples and are not intended to limit the present disclosure. Among the components in the following embodiments, components that are not mentioned in any independent claim describing the broadest concept will be described as optional components. In the drawings, duplicated description for components denoted by the same signs may be omitted. The drawings schematically illustrate each component for easier understanding, and, for example, the shapes and sizes are not exactly shown in some cases.

Embodiment 1

The hydrogen-supplying solution contains a hydrogenated aromatic compound, at least one type of the cation represented by the following Formula (1) or (2):

  (1),

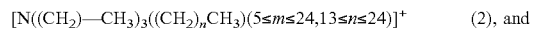  (2), and an anion.

The hydrogenated aromatic compound is a compound in a hydrogen-storing state by binding of hydrogen to the aromatic compound. The "hydrogenated aromatic compound" is prepared by adding hydrogen to at least one carbon-carbon double bond of the aromatic compound and may include a carbon-carbon unsaturated bond in the molecule. The hydrogenated aromatic compound is preferably composed of only carbon and hydrogen. The hydrogenated aromatic compound composed of only carbon and hydrogen is a low polar compound having low polarization of charge in the molecule.

Examples of the compound that can be used as a hydrogenated aromatic compound include methylcyclohexane, 1,2-dimethylcyclohexane, 1,3-dimethylcyclohexane, 1,4-dimethylcyclohexane, tetralin, decalin, methyltetralin, bicyclohexyl, and cyclohexylbenzene. As described above, when these compounds are used as hydrogen storing and supplying means, the compound to which hydrogen is bound and the compound from which hydrogen is desorbed are preferably capable of being treated as compounds belonging to petroleum, such as gasoline, from the viewpoints of melting point, boiling point, combustibility, explosiveness, toxicity, etc. From these viewpoints, the hydrogenated aromatic compound is preferably methylcyclohexane, dimethylcyclohexane, or decalin. The compounds obtained by completely desorbing hydrogen atoms from methylcyclohexane, dimethylcyclohexane, and decalin are toluene, xylene, and naphthalene, respectively.

The above-described hydrogenated aromatic compound has low polarity. Accordingly, for example, a common electrolyte, such as tetraethyl ammonium tetrafluoroborate $(N(CH_3)_4BF_4)$, is substantially insoluble in the above-described hydrogenated aromatic compound. This is probably caused by that the energy necessary for dissociation into a cation and an anion is high due to the short side-chains binding to the cation and the anion and that the energy gain by solvation is low due to the small surface areas of the cation and the anion.

The hydrogen-supplying solution of the present disclosure particularly includes ammonium ions or phosphonium ions having long carbon side chains. Specifically, examples of the cation include $[P((CH_2)_mCH_3)_3((CH_2)_nCH_3)$ $(5 \leq m \leq 24, 13 \leq n \leq 24)]^+$ and $[N((CH_2)_mCH_3)_3((CH_2)_nCH_3)$ $(5 \leq m \leq 24, 13 \leq n \leq 24)]^+$.

As described by the following examples, in the ammonium ions and phosphonium ions, when the number m of carbon atoms is less than 5 or when the number n of carbon atoms is less than 13, the cations have low solubility and are not dissolved at a sufficient concentration. Consequently, sufficient conductivity cannot be imparted to the hydrogenated aromatic compound.

Increases in the numbers m and n enlarge the surface areas that can be solvated and therefore enhance the solubility of the cation. Accordingly, a large number of cations are dissolved in the hydrogen-supplying solution. As a result, the resistance of the hydrogen-supplying solution is reduced to allow a larger amount of current to flow in the hydrogen-supplying solution.

However, in the ammonium ions and phosphonium ions, increases in the numbers m and n increase the molecular weight of the cation to significantly increase the lattice energy and the viscosity of the electrolyte and decrease the solubility of the cation to increase the resistance of the hydrogen-supplying solution. Considering the solubilities of n-alkane in methylcyclohexane and toluene disclosed in the document, "Elise Provost, et. al., "Solubility of some n-Alkanes (C23, C25, C26, C28) in Heptane, Methylcyclohexane, and Toluene", J. Chem. Eng. Data 1998, 43, 745-749", if the number m or n of carbon atoms is higher than 24, the solubility of the cation disadvantageously decreases. Therefore, within the above-mentioned range of the numbers m and n of carbon atoms, appropriate conductivity can be imparted to the hydrogenated aromatic compound to give a hydrogen-supplying solution suitable for electrolysis.

The anion contained in the hydrogen-supplying solution preferably has a bulky structure. This is because that an anion having a bulky substituent increases the substantial ionic radius, which decreases the energy for dissociating into an anion and a cation and is thereby expected to enhance the solubilities of the anion and the cation. For example, $[N(SO_2CF_3)_2]^-$ and $[[(CH_3)_3CCH_2CH(CH_3)CH_2]PO_2]^-$ are preferred anions.

The hydrogen-supplying solution preferably does not contain another polar solvent from the viewpoint of the energy density. The hydrogen-supplying solution not containing another polar solvent can have a high energy density. However, from the viewpoint other than the energy density, for example, from the viewpoint of improving other characteristics that can affect the dehydrogenation, such as the viscosity and resistance of the hydrogen-supplying solution, the hydrogen-supplying solution may contain another polar solvent, for example, at a volume rate of about 10 vol %.

The hydrogen-supplying solution may further contain another compound contributing to the dehydrogenation. Examples of such a compound include quinones. The quinones are, for example, 2,3-dichloro-5,6-dicyano-p-benzoquinone (hereinafter, abbreviated as DDQ) and chloranil. Chloranil is an oxidant that is used in dehydrogenation extracting hydrogen from organic compounds. The document "Peter F. Driscoll, Elise Deunf, Leah Rubin, John Arnold, John B. Kerr, Journal of Electron Society, 160 G3152-G3158 (2013)" suggests that in acetonitrile, DDQ functions as a mediator for electrochemically extracting hydrogen from benzylaniline.

Accordingly, for example, when the hydrogen-supplying solution contains DDQ, it will be possible to extract hydrogen from the hydrogenated aromatic compound in the hydrogen-supplying solution by immersing an anode and a cathode in the hydrogen-supplying solution and applying a voltage between the anode and the cathode to electrochemically cause dehydrogenation. In this case, the hydrogen-supplying solution of the present disclosure has high conductivity even if it does not contain a polar solvent different from the electrolyte containing the cation of the present disclosure. Accordingly, if hydrogen can be extracted, it is judged that hydrogen can be stored at a high energy density.

In the desorbing process and the hydrogen-supplying solution of the present disclosure, thus, the hydrogen-supplying solution contains a hydrogenated aromatic compound and a cation and an anion that can be dissolved in the hydrogenated aromatic compound. Accordingly, if hydrogen can be electrochemically desorbed from the hydrogenated aromatic compound, the hydrogen-supplying solution can have a high energy density by not containing any polar solvent not having desorbable hydrogen atoms.

In the embodiment described above, the hydrogen-supplying solution contains a hydrogenated aromatic compound, but may further contain an aromatic compound. In such a case, the aromatic compound is preferably composed of only carbon and hydrogen. The aromatic compound composed of only carbon and hydrogen is also a low polar compound having low polarization of charge in the molecule. Accordingly, an electrolyte including the cation represented by Formula (1) or (2) can be dissolved also in the aromatic compound, as in the hydrogenated aromatic compound, and can impart conductivity to the aromatic compound. In this case, the hydrogen-supplying solution can store hydrogen by adding hydrogen to the carbon-carbon double or triple bond of the aromatic compound. The hydrogen-supplying solution may further contain a compound contributing to hydrogenation and may thereby electrochemically add hydrogen to the aromatic compound.

EXAMPLES

The results of study on the solubilities of electrolytes in hydrogenated aromatic compounds will now be described.

Example 1

A hydrogenated aromatic compound (10 mL of methylcyclohexane) was weighed in a container, and an electrolyte (0.02 g when it was a solid and 0.2 mL when it was a liquid) was weighed and added to the container, followed by stirring. The electrolyte used was $[N(CH_2CH_3)_4][BF_4]$, $[N((CH_2)_3CH_3)_4][PF_6]$, $[N((CH_2)_3CH_3)_3CH_3][CH_3OSO_3]$, $[Py(CH_3)((CH_2)_3CH_3)][N(SO_2CF_3)_2]$, $[N(C_6H_{11})(CH_3)_3]$ $[N(SO_2CF_3)_2]$, $[P((CH_2)_3CH_3)_3((CH_2)_{11}CH_3)][N(SO_2CF_3)_2]$, $[P((CH_2)_5CH_3)_3((CH_2)_{13}CH_3)][[CH_3)_3CCH_2CH(CH_3)CH_2]_2PO_2]$, or $[P((CH_2)_5CH_3)_3((CH_2)_{13}CH_3)][N(SO_2CF_3)_2]$, wherein Py denotes a pyridinium group.

Subsequently, the dissolution state was visually inspected, and the resistance was further measured for inspecting the degree of mixing or dissolution. Table 1 shows the results. In Table 1, Excellent indicates a resistance value of 50 MΩ or less, and Poor indicates a resistance value of higher than 50 MΩ.

TABLE 1

| Electrolyte | Resistance value |
|---|---|
| [P((CH$_2$)$_5$CH$_3$)$_3$((CH$_2$)$_{13}$CH$_3$)][N(SO$_2$CF$_3$)$_2$] | Excellent |
| [P((CH$_2$)$_5$CH$_3$)$_3$((CH$_2$)$_{13}$CH$_3$)][[(CH$_3$)$_3$CCH$_2$CH(CH$_3$)CH$_2$]$_2$PO$_2$] | Excellent |
| [N(CH$_2$CH$_3$)$_4$][BF$_4$] | Poor |
| [N((CH$_2$)$_3$CH$_3$)$_4$][PF$_6$] | Poor |
| [N((CH$_2$)$_3$CH$_3$)$_3$CH$_3$][CH$_3$OSO$_3$] | Poor |
| [Py(CH$_3$)((CH$_2$)$_3$CH$_3$)][N(SO$_2$CF$_3$)$_2$] | Poor |
| [N(C$_6$H$_{11}$)(CH$_3$)$_3$][N(SO$_2$CF$_3$)$_2$] | Poor |
| [P((CH$_2$)$_3$CH$_3$)$_3$((CH$_2$)$_{11}$CH$_3$)][N(SO$_2$CF$_3$)$_2$] | Poor |

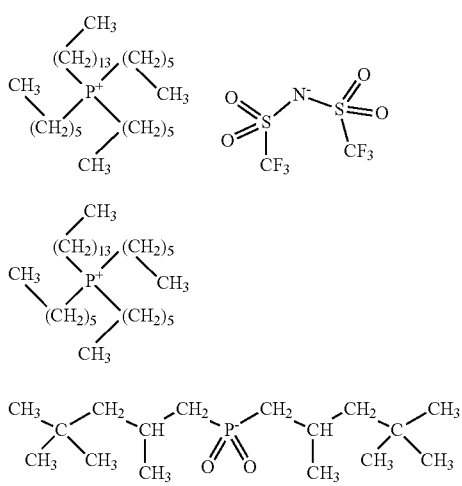

As shown in Table 1, it was demonstrated that only electrolytes represented by chemical formula (3) or (4) are dissolved in and mixed with methylcyclohexane. Both of the electrolytes represented by chemical formula (3) or (4) include the cation represented by Formula (1) wherein m is 5 and n is 13. Since the electrolyte containing the cation represented by Formula (1) wherein m is 3 and n is 11 was not dissolved, it was demonstrated that the lower limits of the numbers m and n are about 5 and 13, respectively.

As described above, increases in the numbers m and n indicating the lengths of alkyl groups in Formulae (1) and (2) enlarge the surface areas that can be solvated and therefore allow to anticipate a reduction in polarity that prevents mixing and to expect an enhancement in solubility. However, if the numbers m and n are too large, the molecular weight of the cation increases, and the lattice energy and the viscosity of the electrolyte are significantly increased. Considering the description in the document, J. Chem. Eng. Data 1998, 43, 745-749, the maximum numbers m and n in Formulae (1) and (2) are estimated to be about 24.

Example 2

An electrolyte [P((CH$_2$)$_5$CH$_3$)$_3$((CH$_2$)$_{13}$CH$_3$)][N(SO$_2$CF$_3$)$_2$] (manufactured by Sigma-Aldrich Co., LLC, purity: 95.0% or more) was added to methylcyclohexane (manufactured by Wako Pure Chemical Industries, Ltd., purity: 98.0% or more), and resistance values were measured within a molar concentration range of 0 mmol/L (pure methylcyclohexane) to 1400.52 mmol/L (molar concentration of pure [P((CH$_2$)$_5$CH$_3$)$_3$((CH$_2$)$_{13}$CH$_3$)][N(SO$_2$CF$_3$)$_2$]) at room temperature with a resistance measuring device (manufactured by Kaise Corporation: KT-2011, maximum measurable resistance: 50 MΩ). FIG. 1 shows the results of the measurement.

Pure methylcyclohexane (the molar concentration of electrolyte: 0 mmol/L) shows unmeasurable resistance (infinite value). It is therefore difficult to cause an electrochemical reaction, such as electrochemical dehydrogenation, in methylcyclohexane. In contrast, the resistance value dramatically decreased with an increase in the concentration of [P((CH$_2$)$_5$CH$_3$)$_3$((CH$_2$)$_{13}$CH$_3$)][N(SO$_2$CF$_3$)$_2$ and decreased to 10.4 MΩ at a concentration of 100 mmol/L. The resistance value gradually decreased in a concentration range of higher than 200 mmol/L and asymptotically reached 1.4 MΩ, which is the resistance value of pure [P((CH$_2$)$_5$CH$_3$)$_3$((CH$_2$)$_{13}$CH$_3$)][N(SO$_2$CF$_3$)$_2$].

The results demonstrated that [P((CH$_2$)$_5$CH$_3$)$_3$((CH$_2$)$_{13}$CH$_3$)][N(SO$_2$CF$_3$)$_2$] is miscible with methylcyclohexane at any proportion to form a uniform solution. It was also demonstrated that if the concentration of the electrolyte is 100 mmol/L or more, the solution has a considerably reduced resistance. Accordingly, the concentration of the electrolyte is preferably 100 mmol/L or more. If the concentration of the electrolyte is 200 mmol/L or more, the volume resistance is further reduced. The concentration of the electrolyte may be therefore 200 mmol/L or more. From the viewpoint of the amount of the electrolyte necessary for reducing the resistance value, a concentration of about 500 mmol/L can provide a solution having sufficiently low resistance. Accordingly, the electrolyte may be used at a concentration of 500 mmol/L.

In this embodiment, quaternary phosphonium salts represented by Formula (1) were used as the examples of the cation. Since quaternary phosphonium salts and quaternary ammonium salts have electrically similar properties, the quaternary ammonium salts represented by Formula (2) are supposed to give similar results.

Embodiment 2

As an example of the electrochemical reaction of an organic hydride, an example of generating hydrogen by dehydrogenation will be described. Specifically, for example, a work electrode and a counter electrode are separated from each other with, for example, a proton conductor to form a receiver of the electrons obtained by dehydrogenation of the organic hydride.

Apparatus Configuration

Figure 2:
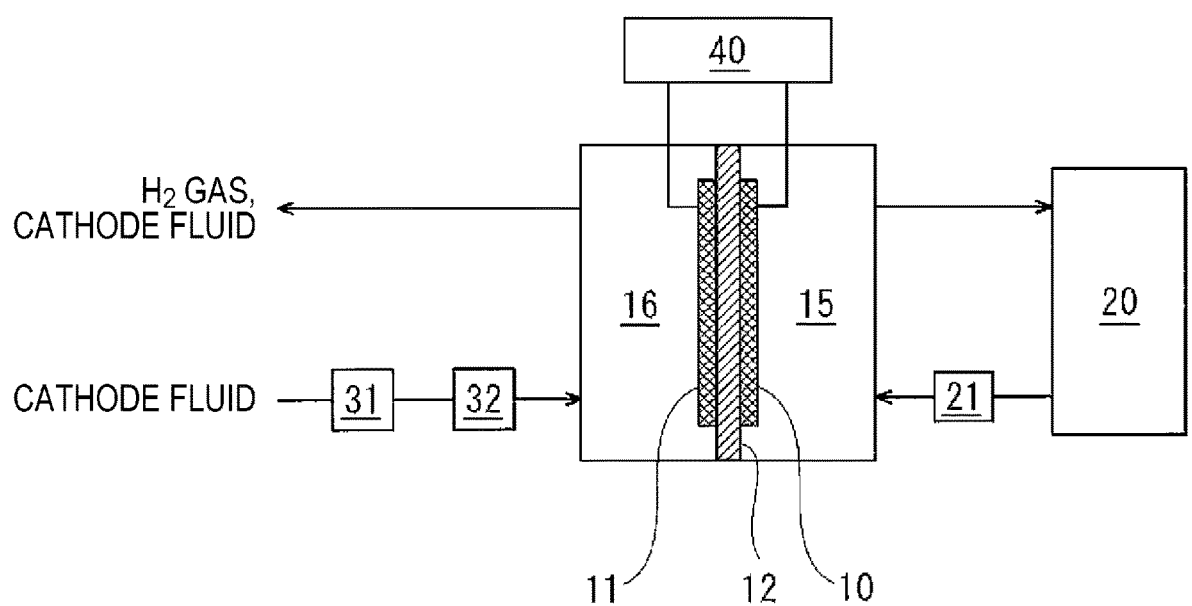
FIG. 2 is a diagram illustrating an example of the dehydrogenation apparatus of Embodiment 2.

FIG. 2 is a diagram illustrating an example of the dehydrogenation apparatus of the embodiment.

In the example shown in FIG. 2, the dehydrogenation apparatus 100 includes an anode 10, a cathode 11, a proton conductor 12, a tank 20, a first server 21, a second server 31, a humidifier 32, and a voltage application device 40.

In the dehydrogenation apparatus 100 of the embodiment, a laminate including the anode 10, the cathode 11, and the proton conductor 12 is disposed so as to divide the inside of a container. The region on the anode 10 side of the container constitutes an anode chamber 15, and a liquid containing a hydrogenated aromatic compound, an electrolyte containing a cation and an anion of the present disclosure, and a quinone flows thereinto. The region on the cathode 11 side of the container constitutes a cathode chamber 16, and a cathode fluid flows thereinto. The configuration is not limited to this. For example, in this example, the cathode fluid is humidified for maintaining the proton conductor 12 in a wet state, but the wet state of the proton conductor 12 may be maintained by supplying moisture from the anode 10 side. In such a case, the cathode fluid is not necessarily allowed to flow into the cathode chamber 16. The anode chamber 15 is an example of the storage chamber of the present disclosure. Examples of the quinone include, but not limited to, chloranil n-mers (n≥1). For example, DDQ may be used.

The anode 10 is an electrode including a dehydrogenation catalyst and may have any configuration as long as it includes a dehydrogenation catalyst. As the catalytic metal of the dehydrogenation catalyst, for example, platinum (Pt) can be used, but the catalytic metal is not limited thereto. Examples of the carrier of the catalyst include carbon.

The cathode 11 is an electrode including a catalyst for reducing protons and may have any configuration as long as it includes a catalyst for reducing protons. As the catalytic metal of the catalyst for reducing protons, for example, platinum (Pt) and ruthenium (Ru) can be used, but the catalytic metal is not limited thereto. Examples of the carrier of the catalyst include carbon.

The proton conductor 12 is disposed between the anode 10 and the cathode 11. Specifically, the anode 10 is disposed on one of the main surfaces of the proton conductor 12, and the cathode 11 is disposed on the other main surface of the proton conductor 12.

The proton conductor 12 may have any configuration as long as it is a member having proton conductivity.

Examples of the proton conductor 12 include solid polymer electrolyte films, such as Nafion (registered trademark, manufactured by E.I. du Pont Nemours and Company), and capping electrolyte films.

Examples of the proton conductor 12 also include inorganic electrolyte films, such as films of yttrium-doped barium zirconate (BZY), a compound composed of iron and tantalum, or a compound mainly composed of stannous pyrophosphate; and inorganic-organic hybrid electrolyte films composed of porous inorganic materials and ionic liquids absorbed therein.

The first server 21 supplies a liquid (hereinafter, occasionally abbreviated to "organic hydride solution") containing a hydrogenated aromatic compound, a chloranil n-mer (n≥1), and an electrolyte containing a cation and an anion of the present disclosure to the anode 10.

The tank 20 contains the organic hydride solution. The organic hydride solution may contain a polar solvent, such as acetonitrile and water, and may be mixed with the aromatic compound generated by dehydrogenation of the organic hydride.

The first server 21 may have any configuration as long as it can supply the above-described liquid to the anode 10. Examples of the first server 21 include a positive-displacement pump.

The hydrogenated aromatic compound in the organic hydride solution may be an alicyclic saturated hydrocarbon having a tertiary carbon atom. The alicyclic saturated hydrocarbon having a tertiary carbon atom may be a monocyclic saturated hydrocarbon having a tertiary carbon atom bearing a saturated hydrocarbon side chain or a polycyclic saturated hydrocarbon.

Examples of the monocyclic saturated hydrocarbon having a tertiary carbon atom bearing a saturated hydrocarbon side chain include methylcyclohexane, 1,2-dimethylcyclohexane, 1,3-dimethylcyclohexane, and 1,4-dimethylcyclohexane. Examples of the polycyclic saturated hydrocarbon include decalin, methyldecalin, 1,2-dimethyldecalin, 1,3-dimethyldecalin, and 1,4-dimethyldecalin. As described above, when these compounds are used as hydrogen storing and supplying means, the compound to which hydrogen is bound and the compound from which hydrogen is desorbed preferably can be treated as compounds belonging to petroleum, such as gasoline, from the viewpoints of melting point, boiling point, combustibility, explosiveness, toxicity, etc. From these viewpoints, the monocyclic saturated hydrocarbon having a tertiary carbon atom bearing a saturated hydrocarbon side chain is preferably methylcyclohexane or dimethylcyclohexane, and the polycyclic saturated hydrocarbon is preferably decalin. The compounds obtained by completely desorbing hydrogen atoms from methylcyclohexane, dimethylcyclohexane, and decalin are toluene, xylene, and naphthalene, respectively.

Figure 3A:
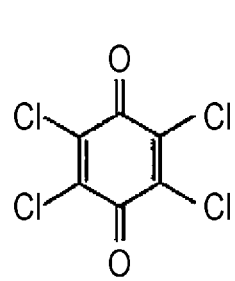
FIGS. 3A to 3C are diagrams illustrating examples of the structural formula of a chloranil n-mer ($n \geq 1$) in an organic hydride solution.
Figure 3B:
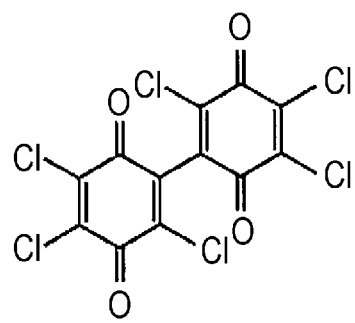
Figure 3C:
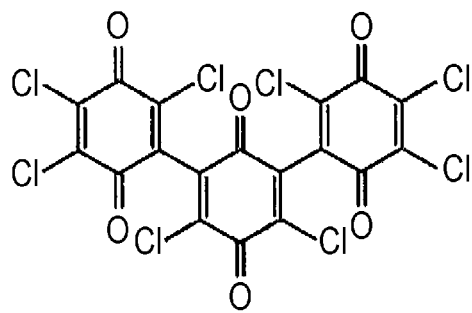

FIGS. 3A to 3C are diagrams illustrating examples of structural formula of the chloranil n-mer (n≥1) in an organic hydride solution. FIG. 3A shows the structural formula of a chloranil monomer; FIG. 3B shows the structural formula of a chloranil dimer; and FIG. 3C shows the structural formula of a chloranil trimer.

The chloranil n-mer (n≥1) in the organic hydride solution functions as a mediator in indirect electrolysis.

Figure 4A:
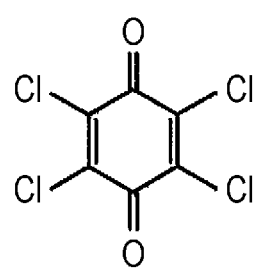
FIGS. 4A and 4B are diagrams illustrating an example of chloranil and an example of hydrogenated chloranil, hydroquinone, respectively.
Figure 4B:
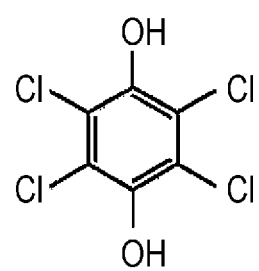

The function of chloranil as a mediator will now be described using a chloranil monomer (hereinafter, referred to as chloranil) as an example of the chloranil n-mer (n≥1) with reference to FIGS. 4A and 4B.

Chloranil (see FIG. 4A) seems to be being activated by electrochemical oxidation, compared to that before the oxidation. The activated chloranil can extract hydrogen from an organic hydride by dehydrogenation. The activated chloranil seems to then bind to the extracted hydrogen to generate a hydroquinone body (see FIG. 4B). The hydroquinone body of the chloranil seems to be then electrochemically oxidized to return to chloranil, and hydrogen seems to be desorbed from the hydroquinone body.

The reactions described above proceed at low temperature (for example, room temperature). That is, the dehydrogenation apparatus 100 of the embodiment can desorb hydrogen from a hydrogenated aromatic compound at low temperature. In addition, chloranil can be electrochemically regenerated from the hydroquinone body of chloranil by hydrogen desorption at low temperature.

The electrolyte in the organic hydride solution includes at least one type of the cations represented by Formula (1) or (2) of the present disclosure and includes an anion.

Examples of the electrolyte include, but not limited to, trihexyltetradecylphosphonium bis(trifluoromethylsulfonyl)imide.

The second server 31 supplies a cathode fluid to the cathode 11 and may have any configuration as long as it can supply the cathode fluid to the cathode 11.

When the proton conductor 12 is, for example, a solid polymer electrolyte film, the solid polymer electrolyte film shows proton conductivity in a wet state. Accordingly, in this case, the dehydrogenation apparatus 100 includes a humidifier 32 for humidifying the cathode fluid. The humidifier 32 may have any configuration as long as it can humidify the cathode fluid.

For example, in the dehydrogenation apparatus 100 of the embodiment, a bubbling system is employed for humidifying the cathode fluid. That is, the humidifier 32 includes a bubbling tank (not shown) for containing liquid water. The cathode fluid is allowed to pass through the water in the bubbling tank and is thereby humidified. In such a case, the second server 31 is a device for adjusting the flow rate of the carrier gas of the bubbling system to be supplied to the water in the bubbling tank. Examples of the second server 31 include a massflow controller and a flow regulating valve.

When an inert gas is used as the carrier gas of the bubbling system, the cathode fluid contains the inert gas. Examples of the inert gas include a nitrogen gas and noble gases, such as an argon gas.

As described above, in the dehydrogenation apparatus 100 of the embodiment, the cathode fluid is bubbled into water to be humidified and is then supplied from the humidifier 32 so as to pass through the cathode chamber 16 and comes into contact with the cathode 11. Consequently, the moisture in the cathode fluid is supplied to the proton conductor 12 from the cathode 11. The proton conductor 12 (for example, solid polymer electrolyte film) can be appropriately maintained in a wet state by thus actively humidifying the cathode fluid.

The voltage application device 40 applies a voltage to the anode 10 and the cathode 11. Specifically, the high-potential side terminal of the voltage application device 40 is connected to the anode 10, and the low-potential side terminal of the voltage application device 40 is connected to the cathode 11. The voltage application device 40 may have any configuration as long as it can apply a desired voltage between the anode 10 and the cathode 11.

Operation

An example of the hydrogen desorption method (operation of the dehydrogenation apparatus 100) of the embodiment will now be described with reference to FIG. 2.

The following operation of the dehydrogenation apparatus 100 may be performed by a control program of a controller (not shown). However, it is not absolutely necessary to perform the following operation with the controller. An operator may partially or wholly perform the operation.

The controller may have any configuration as long as it has a controlling function. The controller includes, for example, an arithmetic circuit and a memory device for storing the control program. Examples of the arithmetic circuit include MPU and CPU. The memory device is, for example, a memory. The controller may be constituted of a single controller performing centralized control or may be constituted of a plurality of controllers performing distributed control by cooperation with each other.

The hydrogen desorption method of the embodiment includes a step of supplying a liquid containing a hydrogenated aromatic compound, a quinone, and an electrolyte containing a cation and an anion of the present disclosure to an anode containing a dehydrogenation catalyst and a step of applying a voltage between the anode and the cathode to desorb hydrogen from the hydrogenated aromatic compound.

Specifically, an organic hydride solution is supplied to an anode chamber 15 from a tank 20 through a supply pipe, and a cathode fluid containing moisture is supplied to a cathode chamber 16 from a humidifier 32 through a supply pipe.

On this occasion, a predetermined direct voltage is applied between the anode 10 and the cathode 11 with a voltage application device 40. Consequently, hydrogen is desorbed from the hydrogenated aromatic compound in the organic hydride solution.

In the anode 10, the hydrogenated aromatic compound in the organic hydride solution releases electrons and hydrogen ions (protons) and converts to an aromatic compound.

The released electrons move to the cathode 11 via the voltage application device 40, whereas the protons move from the proton conductor 12 to the cathode 11.

In the cathode 11, a reduction reaction between protons and electrons is performed to generate a hydrogen gas.

The organic hydride solution passed through the anode chamber 15 contains the hydrogenated aromatic compound and may be returned to the tank 20 through an exhaust pipe as shown in FIG. 2 or may be sent to another tank (not shown). The aromatic compound can be reused as an organic hydride through hydrogenation.

Example 3

In the dehydrogenation apparatus 100 and the hydrogen desorption method of this example, methylcyclohexane (MCH) was used as the hydrogenated aromatic compound; $[P((CH_2)_5CH_3)_3((CH_2)_{13}CH_3)][N(SO_2CF_3)_2]$ (trihexyltetradecylphosphonium bis(trifluoromethylsulfonyl)imide) was used as the electrolyte; a chloranil monomer (hereinafter, referred to as chloranil) was used as the mediator; and an argon gas was used as the carrier gas of the bubbling system.

The tank 20 contained an organic hydride solution prepared so as to contain MCH, the electrolyte, and the chloranil at a weight ratio of 62:21:0.1. That is, the organic hydride solution was prepared at a high concentration by dissolving the chloranil in MCH in a liquid form without using a solvent.

The specifications of the evaluation cell were as follows:
proton conductor 12: Nafion NR-21 (thickness: about 50 µm) having an electrode area of 20-mm square,
anode 10: carbon-supported Pt electrode, and
cathode 11: carbon-supported Pt—Ru electrode.

The environmental temperature of the dehydrogenation apparatus 100 was maintained at room temperature. The organic hydride solution was sent to the anode chamber 15 at a flow rate of 2 ccm, and an argon gas humidified by bubbling was sent to the cathode chamber 16 at a flow rate of 200 sccm.

The exhaust pipe in which the argon gas passed through the cathode chamber 16 flows was provided with a quadrupole mass spectrometer (not shown). The direct voltage applied to the evaluation cell with the voltage application device 40 was gradually increased from 0 V up to 1.1 V.

The experimental conditions described above are mere examples, and the present disclosure is not limited thereto.

Figure 5:
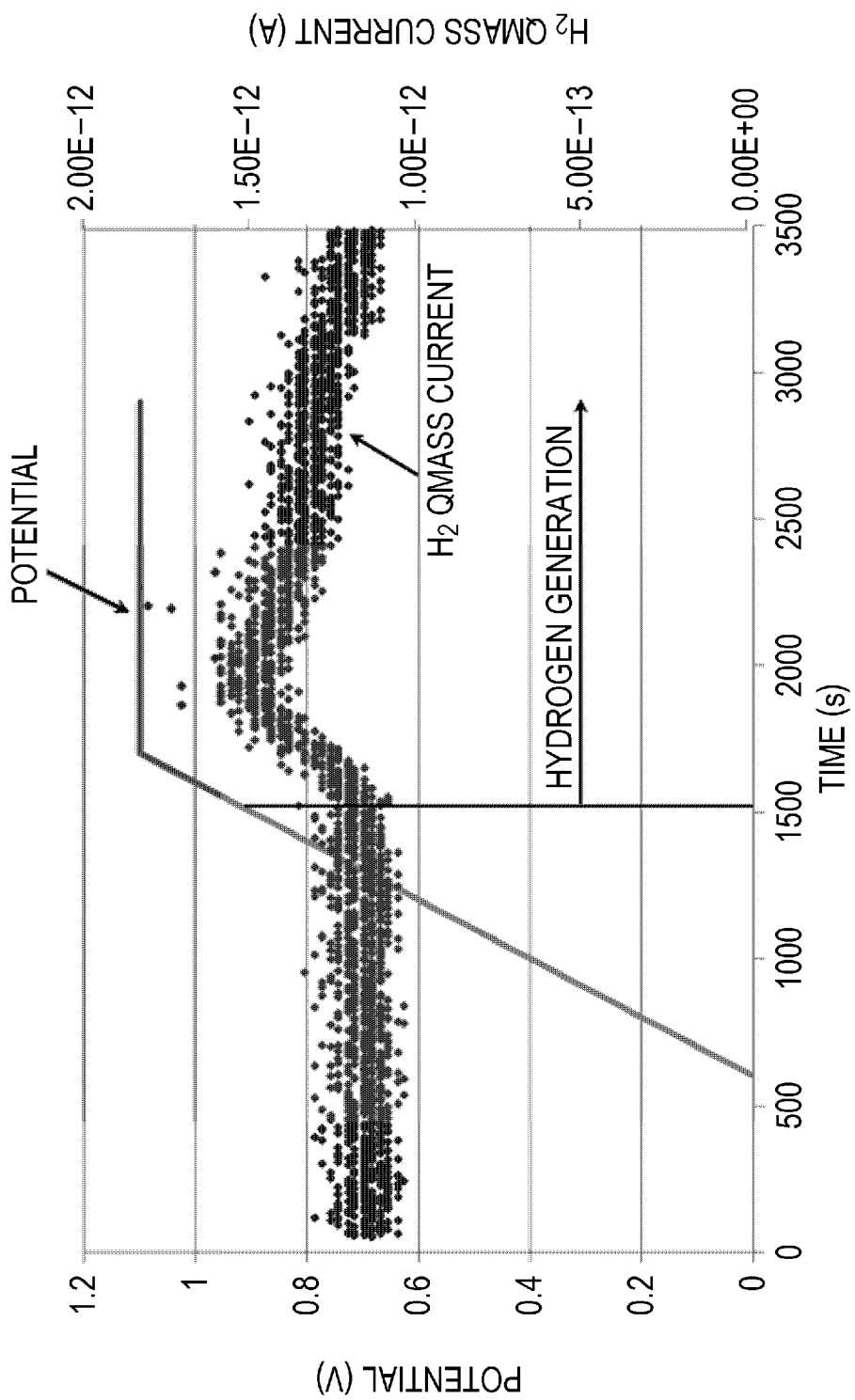
FIG. 5 is a graph showing a relationship between the voltage applied to an evaluation cell and the current value of hydrogen measured with a quadrupole mass spectrometer.

FIG. 5 shows a relationship between the voltage applied to an evaluation cell and the current value of hydrogen measured with a quadrupole mass spectrometer. As shown in FIG. 5, it was observed by gas analysis with a quadrupole mass spectrometer that application of a direct voltage of about 0.9 V with a single cell to the evaluation cell started the generation of hydrogen.

Figure 6:
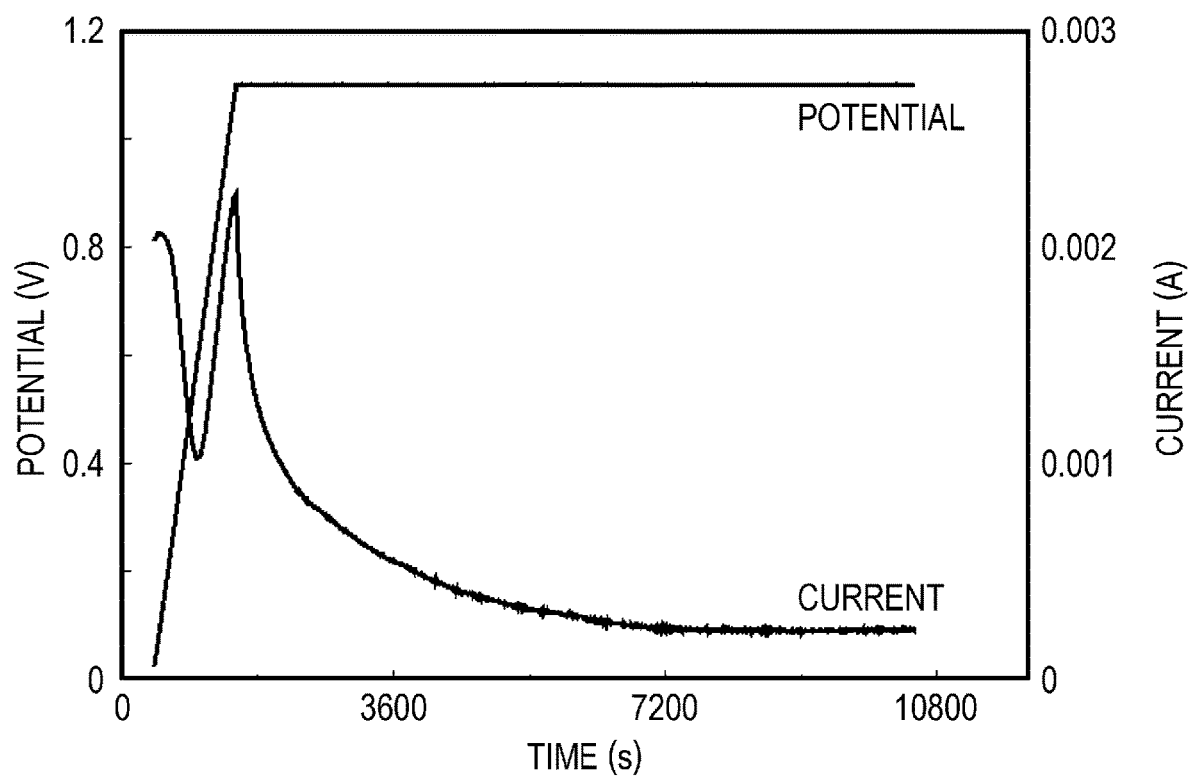
FIG. 6 is a graph showing a relationship between the voltage applied to an evaluation cell and the current flowing in the evaluation cell.

FIG. 6 shows a relationship between the voltage applied to an evaluation cell and the current flowing in the evaluation cell. As shown in FIG. 6, a current continued to flow in the evaluation cell by applying a voltage of 0.9 V or more, which is a voltage showed the generation of hydrogen in FIG. 5. A relatively high current flowing in the evaluation cell at about 0.9 V and a current flowing in the evaluation cell during application of a voltage of lower than 0.9 V are inferred to be currents that flow when an electric double layer is formed on the electrode surface.

Figure 7:
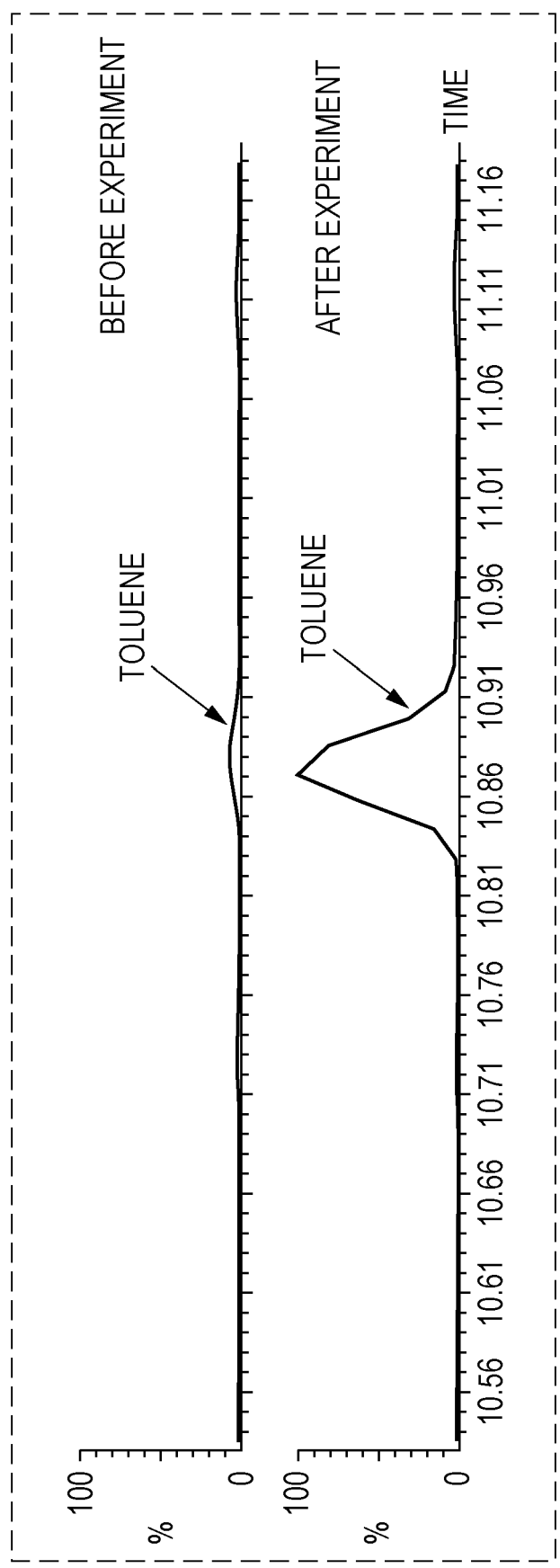
FIG. 7 is a graph showing the results of detection with a gas chromatograph-mass spectrometer of toluene in a solution in an anode chamber before and after the experiment.

FIG. 7 shows the results of detection of toluene in the solution in the anode chamber 15 with a gas chromatograph-mass spectrometer (GC-MS) before and after the experiment. The results after the experiment shown in FIG. 7 are the results of detection of toluene in the solution in the anode chamber with a GC-MS after 30 cycles of the experiment shown in FIG. 5 of applying a voltage to the evaluation cell for 3000 seconds.

As shown in FIG. 7, it was demonstrated that the amount of toluene in the solution in the anode gas increased after the experiment.

Specifically, the amount of toluene in the solution in the anode chamber 15 measured with a GC-MS before the experiment was 3.9 ppm. The amount of toluene in the solution passed through the anode chamber 15 measured with a GC-MS after the experiment was 60.9 ppm, which was 15-fold that before the experiment. Generation of toluene, the product by dehydrogenation of MCH, was confirmed by the experiment described above.

Example 4

Figure 8:
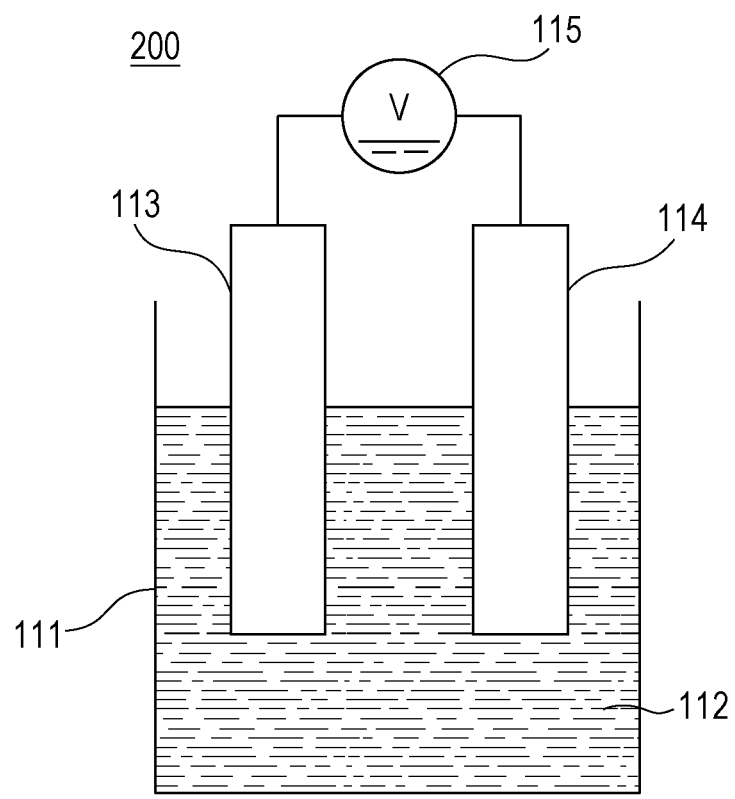
FIG. 8 is a schematic view illustrating an example of the dehydrogenation apparatus used in Example 4.

FIG. 8 is a schematic view illustrating an example of the dehydrogenation apparatus 200 used in the present Example. As shown in FIG. 8, a mixture of 200 mL of acetonitrile (Wako Pure Chemical Industries, Ltd., 75-05-8), trihexyltetradecylphosphonium bis(trifluoromethylsulfonyl)imide (Sigma-Aldrich Co., Ltd. Purity more than 95%), DDQ (Tokyo Chemical Industry Co., Ltd., 84-58-2), and methylcyclohexane (in the drawings, referred to as MCH, Wako Pure Chemical Industries, Ltd., 108-87-2) was uniformly mixed by stirring with a stirrer to prepare a sample liquid 112.

A concentration of trihexyltetradecylphosphonium bis(trifluoromethylsulfonyl)imide in the sample liquid 112 is 0.1 mol/L. A concentration of DDQ in the sample liquid 112 is 6 mmol/L. A concentration of MCH in the sample liquid 112 is 600 mmol/L. The prepared sample liquid was introduced into the airtight container 111, and a counter electrode 113 (Pt) and a work electrode 114 (Pt) connected to a cyclic voltammetry (CV) device 115 were immersed in the sample liquid. A reference electrode (Pt) is used in the present example. The CV device 115 applied a voltage at a sweep rate of 0.5 V/s such that the potential of the work electrode reached +0.4V from −2.0V to perform cyclic voltammetry at normal temperature. When the sample 112 is stirred and is applied 0.28 V to, a change of concentration of toluene in the sample 112 with respect to a voltage application time is measured by GC (Gas Chromatography). A toluene area ratio is used as a value corresponding to the concentration of toluene. The toluene area ratio is a ratio of an area of toluene to the sum of the area of toluene and an area of MCH. The area of toluene and the area of MCH are measured by GC.

Figure 9:
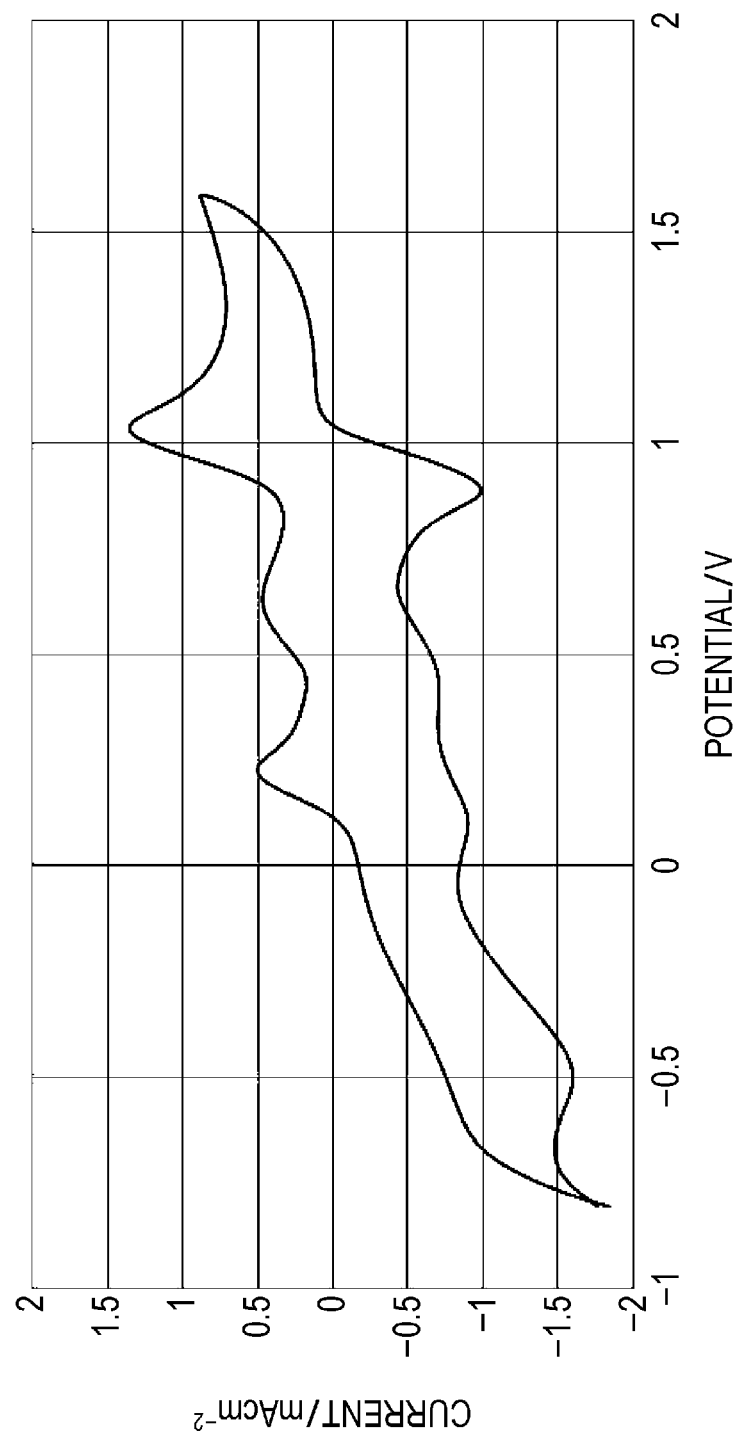
FIG. 9 is an example of a graph collectively showing the results of cyclic voltammetry measurement in Comparative Example 4.
Figure 10:
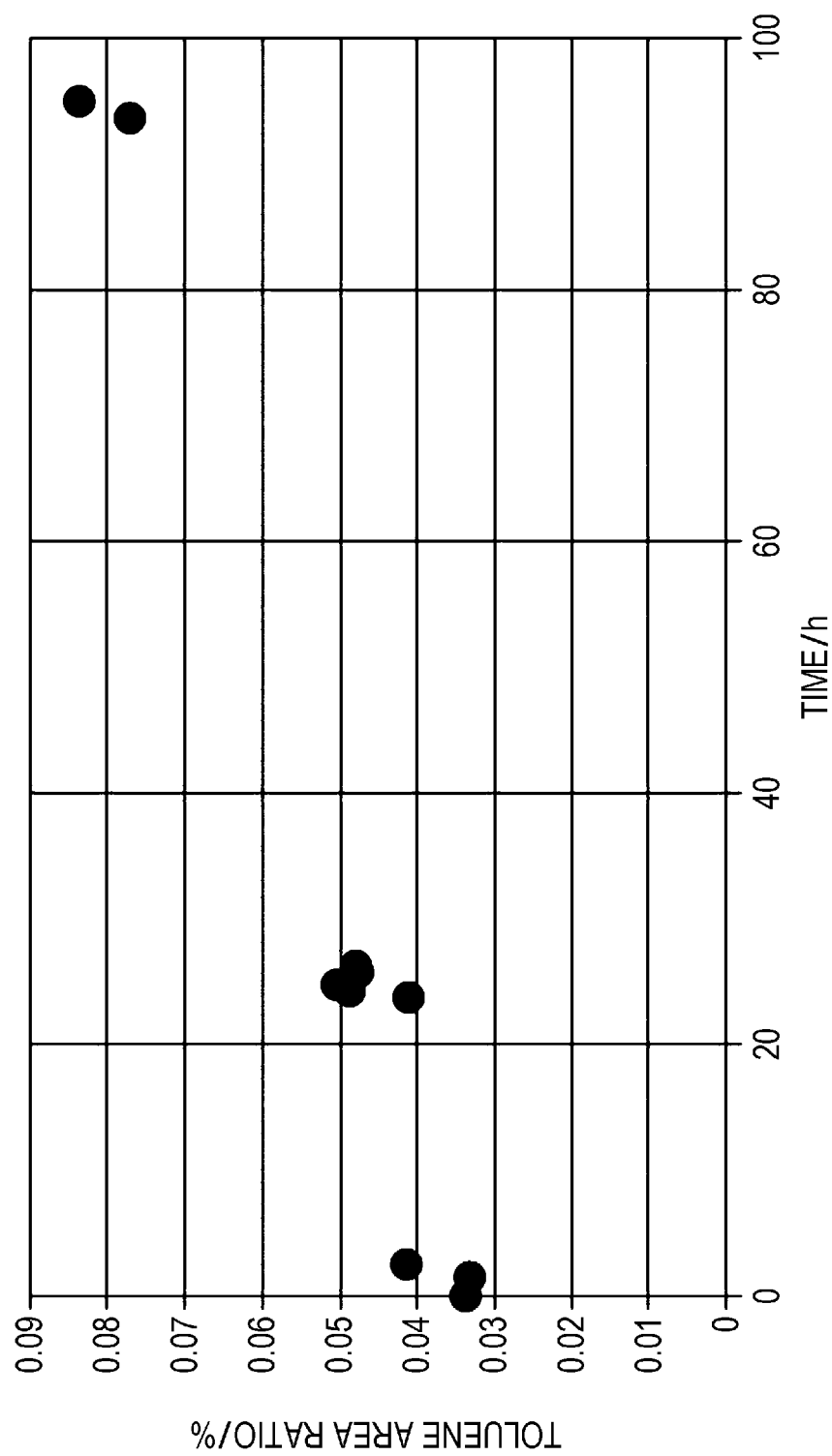
FIG. 10 is an example of a graph collectively showing the results of GC (Gas Chromatography) measurement in Comparative Example 4.

A cyclic voltammetry measurement result in Example 3 is shown in FIG. 9. The measurement results of toluene concentration change are shown in FIG. 10. The result shown in FIG. 9 is modified with standard electrode potential (1.188 V) of the reference electrode (Pt).

As shown in FIG. 9, in the sample containing a monocyclic saturated hydrocarbon having a tertiary carbon atom bearing a saturated hydrocarbon side chain of Example 4, first peaks of oxidation of DDQ are observed at near 0.2 V and 0.6 V, and a second peak of oxidation of DDQ is observed at near 1.0 V. On the reducing side, peaks are observed at near 0.1 V and 0.8 V.

In the first peaks, the peak at 0.2 V is connected to the peak at 0.6 V without largely decreasing the current value. This seems to indicate that one or more reactions other than the oxidation of DDQ continue to occur. In addition, methylcyclohexane is stable compounds and are not oxidized at a voltage of about 0 to 1 V. These results suggest that in the samples of Example 4, DDQ in an oxidized form causes dehydrogenation for extracting hydrogen from methylcyclohexane at normal temperature to generate carbon-carbon double bonds in the methylcyclohexane. Considering that the current value is not decreased much in a voltage range of 0.2 V to 1 V, the dehydrogenation is inferred to be sequentially caused.

The toluene area ratio is increased with the passage of the voltage application time in FIG. 10. It is inferred that MCH undergoes dehydrogenation at room temperature by DDQ in the oxidized form and toluene is formed.

As described above, an organic hydride can be appropriately dehydrogenated by using the electrolyte containing a cation and an anion of the present disclosure.

In the dehydrogenation shown in this embodiment, a quinone (chloranil) was used not as a dehydrogenating agent, but for decreasing the voltage for the dehydrogenation. The quinone as a dehydrogenating agent is not necessarily required in the dehydrogenation.

In the embodiments described above, dehydrogenation of organic hydrides by applying the voltage to the liquid containing organic hydrides was shown as one example of various electrochemical reactions of organic hydrides, but the present disclosure is not limited thereto. For example, an organic hydride may be applied to an electrode reaction of the anode of a fuel cell as fuel in the fuel cell, and may be dehydrogenated from.

The desorbing process, the hydrogen-supplying solution, and the desorbing apparatus of the present disclosure can be used for supply of hydrogen by organic hydrides through various electrochemical reactions and also can be used for storage of hydrogen by organic hydrides through various electrochemical reactions.

What is claimed is:
1. A desorbing process, comprising:
   bringing a solution containing a hydrogenated aromatic compound, at least one of $[P((CH_2)_m CH_3)_3((CH_2)_n CH_3)]^+$ ($5 \leq m \leq 24$, $13 \leq n \leq 24$)]$^+$ and $[N((CH_2)_m CH_3)_3 ((CH_2)_n CH_3)]$ ($5 \leq m \leq 24$, $13 \leq n \leq 24$)]$^+$, and an anion into contact with an anode; and
   desorbing hydrogen from the hydrogenated aromatic compound.
2. The desorbing process according to claim 1, wherein the hydrogenated aromatic compound includes at least one selected from the group consisting of cyclohexane, methylcyclohexane, dimethylcyclohexane, and decalin.
3. The desorbing process according to claim 1, wherein the solution contains $[P((CH_2)_5 CH_3)_3((CH_2)_{13} CH_3)]^+$ or $[N((CH_2)_5 CH_3)_3((CH_2)_{13} CH_3)]^+$ at a concentration of 100 mmol/L or more.
4. The desorbing process according to claim 1, wherein the anion includes at least one of $[N(SO_2 CF_3)_2]^-$ and $[[(CH_3)_3 CCH_2 CH(CH_3)CH_2]PO_2]^-$.
5. The desorbing process according to claim 1, further comprising:
   bringing the solution into contact with a cathode for desorbing hydrogen from the hydrogenated aromatic compound by applying a voltage to the solution.

* * * * *